US00PP32642P3

(12) United States Plant Patent
Hofmann

(10) Patent No.: US PP32,642 P3
(45) Date of Patent: Dec. 15, 2020

(54) ***OSTEOSPERMUM* PLANT NAMED 'INOSTBLPUR'**

(50) Latin Name: *Osteospermum ecklonis*
Varietal Denomination: INOSTBLPUR

(71) Applicant: Silvia Hofmann, Mainz (DE)

(72) Inventor: Silvia Hofmann, Mainz (DE)

(73) Assignee: INNOVAPLANT ZIERPFLANZEN GmbH & Co. KG, Gensingen (DE)

( * ) Notice: Subject to any disclaimer, the term of this patent is extended or adjusted under 35 U.S.C. 154(b) by 0 days.

(21) Appl. No.: 16/873,451

(22) Filed: Apr. 14, 2020

(65) Prior Publication Data

US 2020/0329605 P1 Oct. 15, 2020

(30) Foreign Application Priority Data

Apr. 15, 2019 (CA) ..... PBR 19-9766

(51) Int. Cl.
*A01H 5/02* (2018.01)
*A01H 6/14* (2018.01)

(52) U.S. Cl.
USPC ..... Plt./360
CPC ..... *A01H 6/148* (2018.05)

(58) Field of Classification Search
USPC ..... Plt./360
CPC ..... A01H 6/148
See application file for complete search history.

*Primary Examiner* — Anne Marie Grunberg
(74) *Attorney, Agent, or Firm* — C. Anne Whealy

(57) ABSTRACT

A new and distinct cultivar of *Osteospermum* plant named 'INOSTBLPUR', characterized by its mounding and semi-upright plant habit; moderately vigorous growth habit; freely branching habit; dense and bushy appearance; early and freely flowering habit; long flowering period; large inflorescences with red purple-colored ray florets and dark purple-colored disc florets; and good summer garden performance.

1 Drawing Sheet

Botanical designation: *Osteospermum ecklonis*.
Cultivar denomination: 'INOSTBLPUR'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on Apr. 15, 2019, application number 19-9766. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Osteospermum* plant, botanically known as *Osteospermum ecklonis* and hereinafter referred to by the name 'INOSTBLPUR'.

The new *Osteospermum* plant is a product of a planned breeding program conducted by the Inventor in Heidesheim, Germany. The objective of the breeding program is to create compact and bushy *Osteospermum* plants with numerous large attractive flowers and good summer garden performance.

The new *Osteospermum* plant originated from a cross-pollination made by the Inventor in July, 2014 of a proprietary selection of *Osteospermum ecklonis* identified as code number O 13 201-1 not patented, as the female, or seed, parent with a proprietary selection of *Osteospermum ecklonis* identified as code number O 13 24-1, not patented, as the male, or pollen, parent. The new *Osteospermum* plant was discovered and selected by the Inventor as a single flowering plant from within the progeny of the stated cross-pollination grown in a controlled greenhouse environment in Heidesheim, Germany in April, 2015.

Asexual reproduction of the *Osteospermum* plant by vegetative tip cuttings in Gensingen, Germany since April, 2015 has shown that the unique features of this new *Osteospermum* plant are stable and reproduced true to type in successive generations.

SUMMARY OF THE INVENTION

Plants of the new *Osteospermum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INOSTBLPUR'. These characteristics in combination distinguish 'INOSTBLPUR' as a new and distinct *Osteospermum* plant:

1. Mounding and semi-upright plant habit.
2. Moderately vigorous growth habit.
3. Freely branching habit; dense and bushy appearance.
4. Early and freely flowering habit.
5. Long flowering period.
6. Large inflorescences with red purple-colored ray florets and dark purple-colored disc florets.
7. Good summer garden performance.

Plants of the new *Osteospermum* differ primarily from plants of the female parent selection in the flowering performance as plants of the new *Osteospermum* have better summer garden performance than plants of the female parent selection.

Plants of the new *Osteospermum* differ primarily from plants of the male parent selection in ray floret color as ray florets of plants of the new *Osteospermum* are red purple in color whereas ray florets of plants of the male selection are light pink in color.

Plants of the new *Osteospermum* can be compared to plants of *Osteospermum ecklonis* 'Osoutis', disclosed in U.S. Plant Pat. No. 15,491. In side-by-side comparisons, plants of the new *Osteospermum* differ primarily from plants of 'Osoutis' in the following characteristics:

1. Plants of the new *Osteospermum* are more mounding than and not as upright as plants of 'Osoutis'.
2. Plants of the new *Osteospermum* have larger inflorescences than plants of 'Osoutis'.
3. Plants of the new *Osteospermum* have better summer garden performance than plants of 'Osoutis'.

Plants of the new *Osteospermum* can also be compared to plants of *Osteospermum ecklonis* 'Osectradepu', disclosed in U.S. Plant Pat. No. 20,990. In side-by-side comparisons, plants of the new *Osteospermum* differ primarily from plants of 'Osectradepu' in the following characteristics:

1. Plants of the new *Osteospermum* are more mounding than and not as upright as plants of 'Osectradepu'.
2. Plants of the new *Osteospermum* have larger inflorescences than plants of 'Osectradepu'.
3. Ray florets of plants of the new *Osteospermum* are lighter red purple in color than ray florets of plants of 'Osectradepu'.

BRIEF DESCRIPTION OF THE PHOTOGRAPHS

The accompanying colored photographs illustrate the overall appearance of the new *Osteospermum* plant showing the colors as true as it is reasonably possible to obtain in colored reproductions of this type. Colors in the photographs may differ slightly from the color values cited in the detailed botanical description which accurately describe the colors of the new *Osteospermum* plant.

At the top of the photographic sheet is a side perspective view of a typical flowering plant of 'INOSTBLPUR' grown in a container and at the bottom of the photographic sheet is a close-up view of a typical flowering plant of 'INOSTBLPUR'.

DETAILED BOTANICAL DESCRIPTION

The aforementioned photographs and following observations and measurements describe plants grown during the summer in 15.25-cm containers in a polyethylene-covered greenhouse in St. Thomas, Ontario, Canada and under cultural practices typical of commercial *Osteospermum* production. During the production of the plants, day temperatures averaged 27° C. and night temperatures averaged 15° C. Plants were pinched when planted and were seven weeks from planting rooted cuttings when the photographs and description were taken. In the following description, color references are made to The Royal Horticultural Society Colour Chart, 2007 Edition, except where general terms of ordinary dictionary significance are used.

Botanical classification: *Osteospermum ecklonis* 'INOSTBLPUR'.

Parentage:

*Female parent*.—Proprietary selection of *Osteospermum ecklonis* identified as code number O 13 201-1, not patented.

*Male parent*.—Proprietary selection of *Osteospermum ecklonis* identified as code number O 13 24-1, not patented.

Propagation:

*Type*.—Terminal vegetative cuttings.

*Time to initiate roots, summer*.—About six to eight days at ambient temperatures ranging from 24° C. to 27° C.

*Time to initiate roots, winter*.—About seven to nine days at ambient temperatures ranging from 18° C. to 21° C.

*Time to produce a rooted young plant, summer*.—About four weeks at ambient temperatures ranging from 24° C. to 27° C.

*Time to produce a rooted young plant, winter*.—About five weeks at ambient temperatures ranging from 18° C. to 21° C.

*Root description*.—Medium in thickness, fibrous; typically white in color, actual color of the roots is dependent on substrate composition, water quality, fertilizers, substrate temperature and age of roots.

*Rooting habit*.—Moderately freely branching; medium density.

Plant description:

*Plant and growth habit*.—Mounding to semi-upright plant habit; inflorescences positioned above and beyond the foliar plane on strong peduncles; moderately vigorous growth habit and moderate growth rate.

*Plant height*.—About 21.8 cm.

*Plant diameter*.—About 38.2 cm.

*Lateral branches*.—Quantity per plant: Freely branching habit with about eight primary branches each with about five secondary branches. Primary branches: Length: About 18.7 cm. Diameter: About 5 mm. Internode length: About 8 mm. Secondary branches: Length: About 12.2 cm. Diameter: About 3.8 mm. Internode length: About 1.1 cm. Strength: Strong. Aspect, primary branches: Erect to semi-upright. Aspect, secondary branches: About 45° from primary branch axis. Texture and luster: Glabrous or sparsely pubescent; matte. Color, developing: Close to 145A. Color, developed: Close to 145B.

*Leaf description*.—Arrangement: Alternate, simple. Length: About 6.8 cm. Width: About 3 cm. Shape: Obovate. Apex: Broadly acute to rounded. Base: Attenuate. Margin: Irregularly dentate; indentations shallow to moderate. Texture and luster, upper surface: Sparsely pubescent; moderately glossy. Texture and luster, lower surface: Sparsely pubescent; matte. Venation pattern: Pinnate, arcuate and reticulate. Color: Developing leaves, upper surface: Close to 138A. Developing leaves, lower surface: Lighter than 138A. Fully expanded leaves, upper surface: Close to N137C; venation, close to 139D. Fully expanded leaves, lower surface: Close to 138A; venation, close to 139D. Petioles: Length: About 3.5 cm. Diameter: About 6 mm. Strength: Moderately strong. Texture and luster, upper and lower surfaces: Sparsely pubescent; matte. Color, upper and lower surfaces: Close to 139D.

Inflorescence description:

*Appearance*.—Daisy-type inflorescence form with oblanceolate-shaped ray florets; inflorescences terminal and axillary and positioned above and beyond the foliar plane on strong peduncles; disc and ray florets developing acropetally on a capitulum; inflorescences face mostly upright to slightly outwardly.

*Flowering habit*.—Freely flowering habit with about 41 inflorescences developing per plant at one time.

*Fragrance*.—None detected.

*Flowering response*.—Plants of the new *Osteospermum* flower early and continuously from spring until frost; long flowering period; plants begin flowering about six weeks after planting.

*Inflorescence longevity*.—Inflorescences of plants of the new *Osteospermum* last about one week on the plant; inflorescences persistent.

*Inflorescence buds*.—Height: About 1.2 cm. Diameter: About 9 mm. Shape: Rounded. Texture and luster: Pubescent; matte. Color: Close to 138A.

*Inflorescence size*.—Diameter: Large, about 6.7 cm. Depth (height): About 1.6 cm. Disc diameter: About 1.3 cm.

*Receptacles*.—Diameter: About 1.2 mm. Height: About 5.2 mm. Shape: Cup-shaped. Color: Close to 138A.

*Ray florets*.—Quantity per inflorescence and arrangement: About 22 arranged in two whorls. Length: About 3.4 cm. Width: About 9 mm. Shape: Oblanceolate. Apex: Shallowly emarginate. Base: Narrowly cuneate. Margin: Entire, not undulate. Aspect: Mostly horizontal when fully developed and slightly reflexed. Texture and luster, upper surface: Smooth, glabrous; velvety; matte. Texture and luster, lower surface: Longitudinally ridged, glabrous; slightly glossy. Color: When opening, upper surface: Close to 76C; venation, close to N81B to N81C. When opening, lower surface: Close to 76A; venation, close to N81A. Fully opened, upper surface: Close to 72A; venation, close to N79C; color does not change with development. Fully opened, lower surface: Close to 182D; towards the margins, close to 186C; venation, close to N79B; color does not change with development.

*Disc florets*.—Quantity per inflorescence and arrangement: About 65 spirally arranged in about five whorls at the center of the receptacle. Length: About 6 mm. Diameter, apex: About 1 mm. Diameter, base: About 1 mm. Shape: Tubular; apex, five-pointed with acute points. Texture and luster, inner and outer surfaces: Smooth, glabrous; semi-glossy. Color, immature: Close to 155A; distally, close to N92A. Color, mature: Close to 76B; distally, close to 79B.

*Phyllaries*.—Quantity per inflorescence and arrangement: About 22 arranged in a single whorl. Length: About 8 mm. Width: About 1.5 mm. Shape: Lanceolate. Apex: Acute. Base: Truncate, fused. Margin: Entire. Texture and luster, upper and lower surfaces: Smooth, glabrous; matte. Color, upper and lower surfaces: Close to 138A.

*Peduncles*.—Length: About 5.5 cm. Diameter: About 1.5 mm. Strength: Moderately strong to strong. Aspect: Terminal peduncles, upright; axillary peduncles, about 35° to 45° from vertical. Texture and luster: Sparsely pubescent; minute; matte. Color: Close to 144B.

*Reproductive organs*.—Androecium: Present on disc florets only. Quantity per floret: About five. Filament length: About 4 mm. Filament color: Close to N155A; streaks, close to 185C. Anther length: Less than 1 mm. Anther shape: Lanceolate. Anther color: Close to 202A. Pollen amount: Abundant. Pollen color: Close to 23A. Gynoecium: Present on both ray and disc florets. Pistil length: About 6 mm. Stigma diameter: About 1 mm. Stigma shape: Bi-parted, cleft. Stigma color: Close to 202A. Style length: About 2 mm to 3 mm. Style color: Close to N79B to N79C. Ovary color: Close to 157C.

*Seeds and fruits*.—To date, seed and fruit development has not been observed on plants of the new *Osteospermum*.

Pathogen & pest resistance: To date, plants of the new *Osteospermum* have not been shown to be resistant to pathogens and pests common to *Osteospermum* plants.

Garden performance: Plants of the new *Osteospermum* have been observed to have good summer garden performance and to tolerate rain, wind and to be suitable for USDA Hardiness Zones 9a to 11b.

It is claimed:

1. A new and distinct *Osteospermum* plant named 'INOSTBLPUR' as illustrated and described.

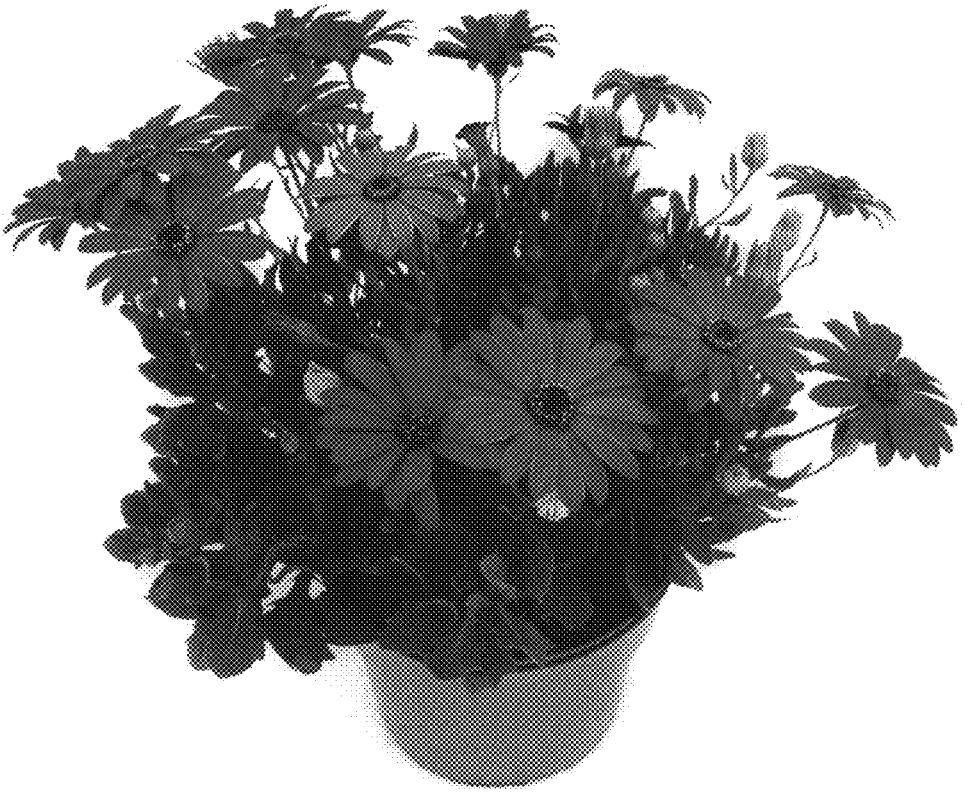
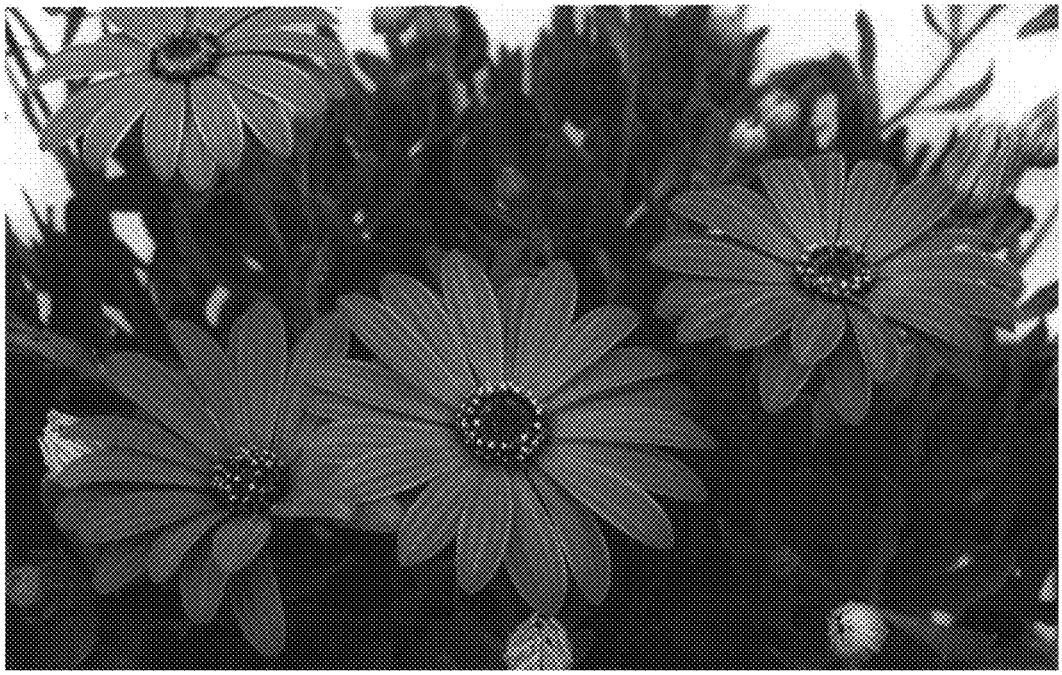

* * * * *